United States Patent
Nakayama et al.

(10) Patent No.: US 8,702,941 B2
(45) Date of Patent: Apr. 22, 2014

(54) METHOD OF ANALYZING HEMOGLOBIN BY ELECTROPHORESIS

(75) Inventors: Yusuke Nakayama, Kyoto (JP); Satoshi Yonehara, Kyoto (JP)

(73) Assignee: ARKARY, Inc., Kyoto (JP)

(*) Notice: Subject to any disclaimer, the term of this patent is extended or adjusted under 35 U.S.C. 154(b) by 250 days.

(21) Appl. No.: 12/978,280

(22) Filed: Dec. 23, 2010

(65) Prior Publication Data

US 2011/0155573 A1 Jun. 30, 2011

Related U.S. Application Data

(60) Provisional application No. 61/297,102, filed on Jan. 21, 2010.

(30) Foreign Application Priority Data

Dec. 25, 2009 (JP) ................................ 2009-296426

(51) Int. Cl.
G01N 27/26 (2006.01)
G01N 27/447 (2006.01)

(52) U.S. Cl.
USPC ........... 204/451; 204/601; 204/600; 204/450; 435/287.1; 422/68.1; 422/82.01; 436/66; 436/67

(58) Field of Classification Search
USPC .............. 204/450, 451, 601, 600; 436/66, 67; 422/68.1, 82.01; 435/287.1, 287.2
See application file for complete search history.

(56) References Cited

U.S. PATENT DOCUMENTS

| | | | | |
|---|---|---|---|---|
| 4,209,372 | A * | 6/1980 | Bluestein et al. | 204/468 |
| 4,209,373 | A | 6/1980 | Bluestein et al. | 204/180 |
| 6,428,704 | B1 * | 8/2002 | Setoguchi et al. | 210/635 |
| 2005/0136548 | A1 | 6/2005 | McDevitt et al. | 436/180 |
| 2005/0274616 | A1 | 12/2005 | Robert et al. | |
| 2009/0134007 | A1 * | 5/2009 | Solis Herrera | 204/157.5 |
| 2009/0200166 | A1 | 8/2009 | Nakayama et al. | |
| 2010/0006436 | A1 | 1/2010 | Oishi et al. | |
| 2010/0155242 | A1 | 6/2010 | Nakayama et al. | 204/451 |
| 2010/0175996 | A1 | 7/2010 | Tanaka et al. | 204/451 |
| 2010/0181199 | A1 | 7/2010 | Sugiyama et al. | |
| 2010/0187110 | A1 * | 7/2010 | Tanaka et al. | 204/451 |

FOREIGN PATENT DOCUMENTS

| | | | |
|---|---|---|---|
| EP | 0733900 | 9/1996 | ........... G01N 27/447 |
| EP | 1582871 | 10/2005 | ........... G01N 33/561 |
| EP | 1596192 A1 | 11/2005 | |
| EP | 2105735 A1 | 9/2009 | |
| EP | 2144056 | 1/2010 | ........... G01N 27/117 |
| EP | 2315015 A1 | 4/2011 | |
| EP | 2623975 A2 | 8/2013 | |
| JP | 3429709 | 4/2000 | |
| JP | 2005-326407 A | 11/2005 | |
| JP | 2008-170351 A | 7/2008 | |
| JP | 2009-186445 A | 8/2009 | |
| WO | WO 85/04251 | 9/1985 | ............. G01N 27/26 |
| WO | WO 2006/132521 | * 12/2006 | |
| WO | WO 2007/112355 | * 10/2007 | |
| WO | WO 2008/029685 | * 3/2008 | |
| WO | WO 2008029684 | 3/2008 | |
| WO | WO 2008029685 | 3/2008 | |
| WO | WO 2008/139866 | 11/2008 | ............. G01N 37/00 |
| WO | 2010/010858 A1 | 1/2010 | |
| WO | WO 2011/001045 | 1/2011 | ........... G01N 27/447 |

OTHER PUBLICATIONS

Chelating Agents (www.biogro.com, downloaded Oct. 24, 2012).*
Mann et al. (Anal. Chem. 2000, 72, 1754-1758).*
EDTA specification sheet (http://www.tau.ac.il/~advanal/EDTA.htm 10/; downloaded Oct. 24, 2012).*
Extended European Search Report dated Apr. 26, 2011 in the corresponding European Application No. 10196917.8.
Frantzen, "Chromatographic and electrophoretic methods for modified hemoglobins", Journal of Chromatography B, 1997, vol. 699, pp. 269-286.
Office Action issued in corresponding Japanese Patent Application No. 2010-288142 dated Aug. 19, 2013.

* cited by examiner

*Primary Examiner* — Jennifer Dieterle
(74) *Attorney, Agent, or Firm* — Morgan, Lewis & Bockius LLP

(57) ABSTRACT

A method for analyzing hemoglobin by electrophoresis, capable of analyzing hemoglobin A1c (HbA1c) and modified hemoglobin with improved accuracy in a shortened analysis time is provided. The method for analyzing hemoglobin by electrophoresis includes performing electrophoresis under conditions in which an acidic substance having two or more carboxyl groups is present in an electrophoresis solution. At least two of the carboxyl groups of the acidic substance each have an acid dissociation constant ($pK_a$) lower than the pH of the electrophoresis solution at the time of analysis.

14 Claims, 4 Drawing Sheets

METHOD OF ANALYZING HEMOGLOBIN BY ELECTROPHORESIS

RELATED APPLICATIONS

This application claims the benefit of Provisional Application No. 61/297,102, filed on Jan. 21, 2010 and Japanese Patent Application No. 2009-296426 filed on Dec. 25, 2009.

FIELD OF THE INVENTION

The present invention relates to a method for analyzing hemoglobin by electrophoresis.

BACKGROUND OF THE INVENTION

Hemoglobin in blood is converted to glycated hemoglobin by reacting with glucose in blood. Among the various types of glycated hemoglobin, hemoglobin A1c (HbA1c), in particular, serves as an important indicator in the diagnosis, treatment, and the like of diabetes. HbA1c is hemoglobin A (HbA0) whose β-chain N terminal valine has been glycated. HbA1c is classified as stable hemoglobin A1c (hereinafter also referred to as "stable A1c" or "s-A1c".) or labile hemoglobin A1c (hereinafter also referred to as "labile A1c" or "L-A1c") according to the stage of the glycation reaction. Labile A1c is HbA0 that has been converted to aldimine by the binding of glucose to its β-chain N terminal valine through a Schiff base linkage. When the labile A1c further undergoes the Amadori rearrangement to become a ketoamine compound, it is called stable A1c. Stable A1c reflects the blood glucose level of the past few months in a subject. Stable A1c may be measured by a measurement method standardized by the Japan Diabetes Society.

Examples of methods for measuring glycated hemoglobin in blood include an immunization method, an enzyme method, affinity chromatography, HPLC, and capillary electrophoresis. The immunization method and the enzyme method are applicable to automated analyzers. Thus, these methods are advantageous in that they can treat a large number of specimens. However, the measurement accuracies of these methods are not sufficient to provide accurate measured values that can serve as blood sugar control indicators and/or complication onset prevention markers for diabetics. Affinity chromatography has low specificity for β-chain N-terminal glycated valine because of its separation principle, so that the measured value also includes the measured value of glycated lysine in Hb molecules. Thus, affinity chromatography results in a low accuracy for HbA1c measurement. HPLC is used widely as a method for measuring glycated hemoglobin in the treatment of diabetics (e.g., JP 3429709 B). However, it requires an expensive dedicated apparatus, and it is difficult to reduce the size and the cost of the apparatus. From the viewpoint of, for example, utilization in group medical examinations, there has been a demand for size reduction of hemoglobin analyzers. However, as described above, for HPLC, it is difficult to satisfy this demand.

On the other hand, in capillary electrophoresis, ions that have gathered on the inner wall of a capillary channel migrate when a voltage is applied, thus causing an electroosmotic flow. This causes the sample to migrate, whereby electrophoresis is performed. In capillary electrophoresis, the size of a capillary electrophoresis apparatus as a whole can be reduced by making the capillary channel shorter and/or configuring a part of the capillary electrophoresis apparatus as a microchip, for example. As a method for analyzing HbA1c according to capillary electrophoresis, a method using a capillary tube having an anionic layer laminated on its inner wall has been reported, for example (e.g., WO 2008/029684 A1 and WO 2008/029685 A1).

SUMMARY OF THE INVENTION

The present invention provides a method for analyzing hemoglobin in a sample solution containing hemoglobin by electrophoresis, including: performing electrophoresis of the sample solution under conditions in which an acidic substance having two or more carboxyl groups is present in an electrophoresis solution. At least two of the carboxyl groups of the acidic substance each have an acid dissociation constant ($pK_a$) lower than a pH of the electrophoresis solution at the time of analysis.

In the method of the present invention, it is preferable that two of the carboxyl groups of the acidic substance each have an acid dissociation constant ($pK_a$) lower than the pH of the electrophoresis solution at the time of analysis.

In the method of the present invention, it is preferable that: the electrophoresis solution contains a buffer and a separation enhancing agent; and the separation enhancing agent contains the acidic substance.

In the method of the present invention, it is preferable that the two or more carboxyl groups of the acidic substance each have an acid dissociation constant ($pK_a$) lower than the pH of the electrophoresis solution at the time of analysis by 0.7 or more.

In the method of the present invention, it is preferable that: the electrophoresis solution contains a buffer; and an acid dissociation constant ($pK_a$) of the buffer responsible for its buffer capacity is equal to or greater than a value obtained by subtracting 0.3 from the pH of the electrophoresis solution at the time of analysis.

In the method of the present invention, it is preferable that: the electrophoresis solution contains a buffer and a separation enhancing agent; the separation enhancing agent contains the acidic substance; and a difference obtained by subtracting a second dissociation constant ($pK_{a2}$) of the acidic substance in the separation enhancing agent from an acid dissociation constant ($pK_a$) of the buffer responsible for its buffer capacity is 0.2 or more.

In the method of the present invention, it is preferable that the difference between a pH of the sample solution containing hemoglobin and the pH of the electrophoresis solution is less than 0.3.

In the method of the present invention, it is preferable that the acidic substance has a cyclohexane ring.

In the method of the present invention, it is preferable that separation of hemoglobin by the electrophoresis is carried out in a separation capillary channel.

The method of the present invention preferably is carried out using a continuous sample introduction method for introducing a sample solution containing hemoglobin continuously to the separation capillary channel.

The method of the present invention may be configured so that: the separation capillary channel is formed on a microchip; and the electrophoresis is microchip electrophoresis.

The method of the present invention may be configured so that: the separation capillary channel is a capillary tube; and the electrophoresis is capillary electrophoresis.

In the method of the present invention, it is preferable that the hemoglobin is hemoglobin A1c.

In the method of the present invention, it is preferable that the hemoglobin A1c is at least one of stable hemoglobin A1c and labile hemoglobin A1c.

In the method of the present invention, it is preferable that the hemoglobin is at least one kind of modified hemoglobin selected from the group consisting of carbamylated hemoglobin, aldehydated hemoglobin, and acetylated hemoglobin.

Furthermore, the present invention provides a separation enhancing agent to be used in the method according to the present invention. The separation enhancing agent contains an acidic substance having two or more carboxyl groups. At least two of the carboxyl groups of the acidic substance each have an acid dissociation constant ($pK_a$) lower than a pH of the electrophoresis solution at the time of analysis. In the separation enhancing agent of the present invention, preferred conditions and configuration are the same as those of the method for analyzing hemoglobin according to the present invention.

Still further, the present invention provides an electrophoresis solution reagent containing the separation enhancing agent to be used in the method according to the present invention. In the electrophoresis solution reagent of the present invention, preferred conditions and configurations are the same as those of the method for analyzing hemoglobin according to the present invention.

Still further, the present invention provides a microchip to be used in the method according to the present invention. The microchip includes: a separation capillary channel: and a plurality of liquid reservoirs. The liquid reservoirs commune with the separation capillary channel, and at least one of the separation capillary channel and the liquid reservoirs contains an electrophoresis solution. The electrophoresis solution contains an acidic substance having two or more carboxyl groups. At least two of the carboxyl groups of the acidic substance each have an acid dissociation constant ($pK_a$) lower than a pH of the electrophoresis solution at the time of analysis. In the microchip of the present invention, preferred conditions and configurations are the same as those of the method for analyzing hemoglobin according to the present invention.

Still further, the present invention provides a reagent to be used in the method according to the present invention. The reagent contains the separation enhancing agent according to the present invention. In addition to the separation enhancing agent, the reagent according to the present invention may further contain an electrophoresis solution, a buffer, an additive, a surfactant, a stabilizing agent, and the like, for example. The reagent of the present invention may be used as an electrophoresis solution reagent, a diluent reagent, a sample solution reagent, or the like, for example.

The present invention also provides an analysis kit including the reagent according to the present invention. The analysis kit of the present invention includes the separation enhancing agent to be used in the method of the present invention. The separation enhancing agent contains an acidic substance having two or more carboxyl groups, and at least two of the carboxyl groups of the acidic substance each have an acid dissociation constant ($pK_a$) lower than the pH of the electrophoresis solution at the time of analysis. In other words, the analysis kit of the present invention includes the separation enhancing agent of the present invention.

DETAILED DESCRIPTION

Figure 1A:
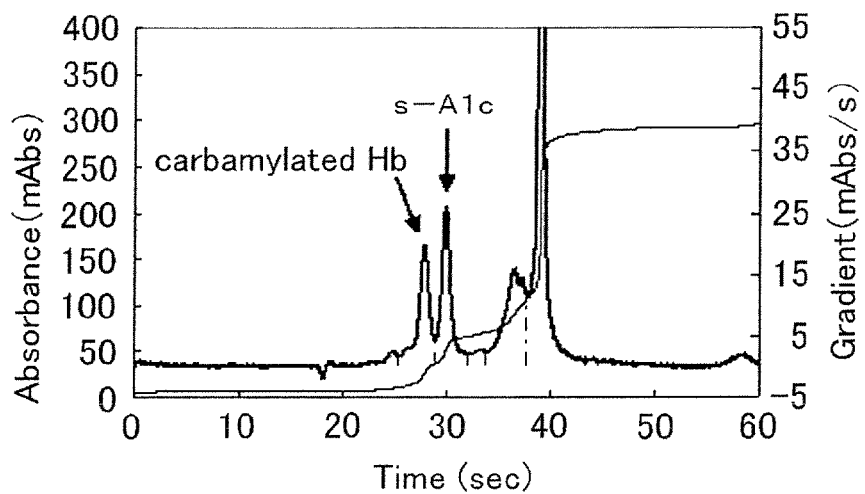
FIGS. 1A to 1C are graphs showing the results of hemoglobin detection in Example 1.

Hereinafter, the present invention will be described in detail. The term "hemoglobin" hereinafter is abbreviated as "Hb".

The method of the present invention is, as described above, a method for analyzing Hb in a sample solution containing hemoglobin by electrophoresis, including: performing electrophoresis of the sample solution under conditions in which an acidic substance having two or more carboxyl groups is present in an electrophoresis solution. At least two of the carboxyl groups of the acidic substance each have an acid dissociation constant ($pK_a$) lower than a pH of the electrophoresis solution at the time of analysis. The method of the present invention is not particularly limited, and the electrophoresis preferably is, for example, capillary electrophoresis or microchip electrophoresis, as will be described below.

In the present invention, the electrophoresis solution refers to a solution used for separating Hb through electrophoresis by applying a voltage thereto. The electrophoresis solution can be classified as an electrophoresis solution before electrophoresis or an electrophoresis solution at the time of electrophoresis, for example. In the present invention, the electrophoresis solution before electrophoresis can be referred to as the "electrophoresis solution before analysis", and the electrophoresis solution at the time of electrophoresis can be referred to as the "electrophoresis solution at the time of analysis". The expression "before electrophoresis" or "before analysis" means before applying a voltage to the electrophoresis solution, for example. The expression "at the time of electrophoresis" or "at the time of analysis" means the state where a voltage is being applied to the electrophoresis solution and a sample has been added to the electrophoresis solution, for example. Although the electrophoresis solution at the time of analysis contains the acidic substance, the electrophoresis solution before analysis either may or may not contain the acidic substance. The electrophoresis solution before analysis and the electrophoresis solution at the time of analysis may contain a buffer and the like, for example.

The acidic substance needs to be present in the electrophoresis solution at the time of analysis. Thus, the acidic substance may be added in advance to the electrophoresis solution before analysis, or may be added in advance to a sample solution containing Hb, for example. In the former case, a solution containing the acidic substance preferably is used as the solution filling the separation capillary channel before analysis, for example. Examples of the separation capillary channel include a capillary tube and a capillary channel. On the other hand, in the latter case, the acidic substance may be added directly to a liquid sample such as a hemolyzed sample, or may be added in advance to a solvent for diluting a sample, as will be described below, for example.

The acidic substance has two or more carboxyl groups, as described above. The number of carboxyl groups in the acidic substance is, for example, 2 to 6, preferably 2 to 4.

The acidic substance may further have a functional group(s) other than the carboxyl groups, for example. The functional group(s) other than the carboxyl groups is not particularly limited, and examples thereof include a hydrogen atom, amino groups, hydroxy groups, alkyl groups having 1 to 5 carbon atoms, alkoxy groups having 1 to 5 carbon atoms, and alkylthio groups having 1 to 5 carbon atoms. In the functional group, one or more hydrogen atoms may be substituted with an arbitrary substituent(s), for example. Examples of the substituent include halogen groups such as a fluoro group, a bromo group, a chloro group, fluorine, and an iodine group. Among them, a fluoro group is preferred.

The acidic substance has two or more carboxyl groups, and the carboxyl groups each have an acid dissociation constant ($pK_a$). In the present invention, at least two of the carboxyl groups have an acid dissociation constant ($pK_a$) in the range from, for example, 2 to 5, preferably 2 to 4.

The acid dissociation constant ($pK_a$) of each of the two or more carboxyl groups of the acidic substance preferably is lower than the pH of the electrophoresis solution at the time of analysis by 0.5 or more, more preferably by 0.7 or more, and still more preferably by 1.0 or more.

Specific examples of the acidic substance include carboxylic acids and amino acids.

The carboxylic acids are, for example, dicarboxylic acid, tricarboxylic acid, tetracarboxylic acid, pentacarboxylic acid, hexacarboxylic acid, heptacarboxylic acid, octacarboxylic acid, nonacarboxylic acid, and decacarboxylic acid. Among them, dicarboxylic acid, tricarboxylic acid, tetracarboxylic acid, pentacarhoxylic acid, and hexacarboxylic acid are preferred. One kind of carboxylic acid may be used, or two or more kinds of carboxylic acids may be used, for example.

Examples of the carboxylic acid include aliphatic carboxylic acids and carbocyclic carboxylic acids. Examples of the aliphatic carboxylic acids include fumaric acid and D-tartaric acid, and D-tartaric acid is preferred. Examples of the carbocyclic carboxylic acids include cyclohexanecarboxylic acids.

The cyclohexanecarboxylic acids have a cyclohexane ring. Preferred cyclohexanecarboxylic acids are: compounds represented by the following general formula (1); tautomers and stereoisomers thereof; and salts, solvates and hydrates thereof, for example.

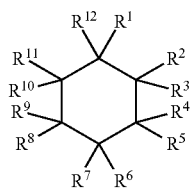

(1)

The general formula (1) has at least two carboxyl groups, and in the general formula (1), $R^1$ to $R^{12}$ are the same or different functional groups. Among $R^1$ to $R^{12}$, at least two are functional groups having at least one carboxyl group and/or at least one is a functional group having at least two carboxyl groups. The former, i.e., the functional groups having at least one carboxyl group, is a carboxyl group and a carboxyalkyl group, for example. In the carboxyalkyl group, the alkyl group moiety has, for example, 1 to 5 carbon atoms, preferably 1 carbon atom. Specific examples of the carboxyalkyl group include —CH$_2$COOH. The latter, i.e., the functional group having at least two carboxyl groups, is a bis(carboxyalkyl)amino group, for example. In the bis(carboxyalkyl) amino group, the alkyl group moiety has, for example, 1 to 5 carbon atoms, preferably 1 carbon atom. Specific examples of the bis(carboxyalkyl)amino group include —N(CH$_2$COOH)$_2$. Specific examples of the functional group include, in addition to the functional groups containing a carboxyl group(s): a hydrogen atom; an amino group; an alkyl group having 1 to 5 carbon atoms; an alkoxy group having 1 to 5 carbon atoms; and an alkylthio group having 1 to 5 carbon atoms. In $R^1$ to $R^{12}$, one or more hydrogen atoms may be substituted with an arbitrary substituent(s). Among the hydrogen atoms and the substituents in $R^1$ to $R^{12}$, at least two may be substituted with carboxyl groups. The substituent is not particularly limited, and examples thereof include a carboxyl group, an acyl group, an amino group, an alkyl group, and a hydroxyl group. The hydroxyl group may be isomerized and present in the form of an oxo group (═O), for example. The hydrogen atom in the substituent may be substituted with a substituent such as a carboxyl group, an amino group, a hydroxyl group, or the like, for example.

The alkyl groups are not particularly limited, and examples thereof include a methyl group, an ethyl group, a n-propyl group, an isopropyl group, a n-butyl group, an isobutyl group, a sec-butyl group, a tert-butyl group, a n-pentyl group, an isopentyl group, a neopentyl group, and a tert-pentyl group. The same applies to groups including an alkyl group in their structures, such as alkoxy groups and alkylthio groups. In the alkyl group, one or more hydrogen atoms may be substituted with an arbitrary substituent(s), for example. The substituent in the alkyl group is not particularly limited, and examples thereof include the above-described substituents.

The alkoxy groups are not particularly limited, and examples thereof include a methoxy group, an ethoxy group, an n-propoxy group, and an isopropoxy group. In the alkoxy group, one or more hydrogen atoms may be substituted with an arbitrary substituent(s), for example. The substituent in the alkoxy group is not particularly limited, and examples thereof include the above-described substituents.

The alkylthio groups are not particularly limited, and examples thereof include a methylthio group, an ethylthio group, an n-propylthio group, and an isopropylthio group. In the alkylthio group, one or more hydrogen atoms may be substituted with an arbitrary substituent(s), for example. The substituent in the alkylthio group is not particularly limited, and examples thereof include the above-described substituents.

As to $R^1$ to $R^{12}$, specific examples of the functional group having a carboxyl group(s) are not particularly limited, and include a carboxyl group (—COOH), the above-described carboxyalkyl group, and the above-described bis(carboxyalkyl)amino group. As the carboxyalkyl group, —CH$_2$—COOH is preferred. As the bis(carboxyalkyl)amino group, —N—(CH$_2$COOH)$_2$ is preferred.

As the cyclohexanecarboxylic acids, specifically, trans-1,2-cyclohexanediamine-N,N,N',N' tetraacetic acid (CyDTA), 1,1-cyclohexanediacetic acid, (1α,2α,4α)-1,2,4-cyclohexanetricarboxylic acid, 1,2,3,4,5,6-cyclohexanehexacarboxylic acid monohydrate, and the like are preferred, for example. One kind of cyclohexanecarboxylic acid may be used, or two or more kinds of cyclohexanecarboxylic acids may be used in combination.

Examples of the above-described amino acids include aspartic acid and glutamic acid. Among them, glutamic acid is preferred. One kind of amino acid may be used, or two or more kinds of amino acids may be used in combination.

As described above, the acidic substance has two or more carboxyl groups, and the carboxyl groups each have an acid dissociation constant ($pK_a$). At least two of the carboxyl groups have an acid dissociation constant ($pK_a$) in the range from, for example, 2 to 5, preferably 2 to 4. Examples of the acidic substance with acid dissociation constants falling within the above-described range include CyDTA, (1α,2α, 4α)-1,2,4-cyclohexanetricarboxylic acid, L-glutamic acid, D-tartaric acid, L-tartaric acid, fumaric acid, citric acid, aspartic acid, phthalic acid, and D-malic acid.

The acid dissociation constant ($pK_a$) of each of the two or more carboxyl groups of the acidic substance preferably is lower than the pH of the electrophoresis solution at the time of analysis. More preferably, it is lower than the pH of the electrophoresis solution at the time of analysis by 0.5 or more, still more preferably by 0.7 or more, and particularly preferably by 1.0 or more. Such an acidic substance is not particularly limited, and examples thereof include CyDTA, D-tartaric acid, fumaric acid, and aspartic acid. Such an acidic substance also can be used as a metal chelating agent, for example. With the use of such a metal chelating agent, it is possible to remove, for example, ions such as calcium ions and magnesium ions in a sample. Furthermore, by removing these ions, it is possible to inhibit the agglutination of anionic group-containing compounds to be described below, for example.

The electrophoresis solution may contain any one of the above-described acidic substances, or may contain two or more of the above-described acidic substances. The combination of the acidic substances and the proportion of each acidic substance are not particularly limited, and they can be set as appropriate.

The concentration of the acidic substance in the electrophoresis solution is not particularly limited, and is, for example, 0.1 to 100 mmol/l, preferably 0.1 to 50 mmol/l, more preferably 0.5 to 10 mmol/l, and still more preferably 1 to 5 mmol/l.

The electrophoresis solution may contain, for example, a separation enhancing agent and a buffer, and the separation enhancing agent may contain the acidic substance.

In addition to the acidic substance, the separation enhancing agent may further contain arbitrary substances, for example. The combination of the substances and the proportion of each substance are not particularly limited, and they can be set as appropriate.

The separation enhancing agent needs to be present in the electrophoresis solution at the time of analysis, for example. Thus, the separation enhancing agent may be added in advance to the electrophoresis solution before analysis, or may be added in advance to the sample solution, for example. In the former case, a solution containing the separation enhancing agent preferably is used as the solution filling the separation capillary channel before analysis, for example. Examples of the separation capillary channel include a capillary tube and a capillary channel. On the other hand, in the latter case, the separation enhancing agent may be added directly to the sample, or may be added in advance to a solvent for diluting the sample, as will be described below, for example.

Examples of the buffer include conventionally known buffer substances. Specific examples of the buffer substances include: inorganic acids such as phosphoric acid and boric acid; organic acids such as L-tartaric acid, acetic acid, maleic acid, malonic acid, phthalic acid, citric acid, formic acid, lactic acid, benzoic acid, succinic acid, propionic acid, malic acid, glutaric acid, tris(hydroxymethyl)aminomethane (Tris), morpholinoethanesulfonic acid (MES), N-(2-acetamido)iminodiacetic acid (ADA), N-(2-acetamido)-2-aminoethanesulfonic acid (ACES), N,N-bis(2-hydroxyethyl)-2-aminoethanesulfonic acid (BES), 3-morpholinopropanesulfonic acid (MOPS), N-tris(hydroxymethyl)methyl-2-aminoethanesulfonic acid (TES), and 2-(4-(2-hydroxyethyl)-1-piperazinyl)ethanesulfonic acid (HEPES); and amino acids such as cysteine, tyrosine, histidine, lysine, and arginine. The electrophoresis solution may contain any one of the above-described buffer substances as the buffer, or may contain two or more of the above-described buffer substances as the buffers. The combination of the buffer substances and the proportion of each buffer substance are not particularly limited, and they can be set as appropriate. When the electrophoresis solution contains a buffer and a separation enhancing agent, the buffer may be a buffer substance other than the acidic substance or may be the acidic substance, for example.

The buffer needs to be present in the electrophoresis solution at the time of analysis, for example. Thus, the buffer may be added in advance to the electrophoresis solution before analysis, or may be added in advance to the sample solution, for example. In the former case, a solution containing the buffer preferably is used as the solution filling the separation capillary channel before analysis, for example. Examples of the separation capillary channel include a capillary tube and a capillary channel. On the other hand, in the latter case, the buffer may be added directly to the sample, or may be added in advance to a solvent for diluting the sample, as will be described below, for example. Preferably, the buffer is added in advance to the electrophoresis solution before analysis, for example. By adding the buffer to the electrophoresis solution before analysis, the difference between the pH of the sample solution and the pH of the electrophoresis solution before analysis can be set in the range to be described below, for example.

The acid dissociation constant ($pK_a$) of the buffer is not particularly limited, and is, for example, 4.5 to 6, preferably 4.5 to 5.5. Examples of the buffer having an acid dissociation constant within the above-described range include L-tartaric acid, citric acid, glutaric acid, succinic acid, acetic acid, phthalic acid, malonic acid, maleic acid, malic acid, and propionic acid.

When the buffer has a plurality of acid dissociation constants ($pK_a$) the acid dissociation constant ($pK_{an}(B)$) of the buffer responsible for its buffer capacity means, for example, among the acid dissociation constants ($pK_a$) of the buffer, the one closest to the pH (X) of the electrophoresis solution at the time of analysis. When the buffer has one acid dissociation constant ($pK_a$), for example, the acid dissociation constant is the acid dissociation constant ($pK_{an}(B)$) of the buffer responsible for its buffer capacity. Among the acid dissociation constants ($pK_a$) of the buffer, the acid dissociation constant ($pK_{an}(B)$) of the buffer responsible for its buffer capacity preferably is equal to or greater than a value obtained by subtracting 0.3 from the pH of the electrophoresis solution at the time of analysis, for example. That is, assuming that the pH of the electrophoresis solution at the time of analysis is "X", the acid dissociation constant ($pK_{an}(B)$) preferably is [X-0.3] or more, for example.

The difference obtained by subtracting the pH (X) of the electrophoresis solution at the time of analysis from the acid dissociation constant ($pK_{an}(B)$) responsible for the buffer capacity of the buffer is, for example, −0.3 or more. Examples of the buffer having an acid dissociation constant within such a range include L-tartaric acid, glutaric acid, acetic acid, phthalic acid, malic acid, and propionic acid.

The acid dissociation constant ($pK_{an}(B)$) responsible for the buffer capacity of the buffer preferably is higher than the acid dissociation constants ($pK_a$) of the at least two carboxyl groups of the acidic substance in the separation enhancing agent, for example. The difference between the acid dissociation constant ($pK_{an}(B)$) responsible for the buffer capacity of the buffer and each of the acid dissociation constants ($pK_a(A)$) of the at least two carboxyl groups of the acidic substance in the separation enhancing agent, i.e., [$pK_{an}(B)-pK_a$ (A)] is, for example, 0.2 or more, preferably 0.5 or more, and more preferably 0.7 or more. Specifically, the difference between the acid dissociation constant ($pK_{an}(B)$) responsible for the buffer capacity of the buffer and a second acid dissociation constant ($pK_{a2}$) of the acidic substance in the separation enhancing agent, i.e., [$pK_{an}(B)$-$pK_{a2}$] is, for example, 0.2 or more, preferably 0.5 or more, and more preferably 0.7 or more. The combination of the buffer and the acidic substance satisfying such a relationship is not particularly limited, and examples thereof include the combinations of; L-tartaric acid and CyDTA; L-tartaric acid and L-glutamic acid; malic acid and CyDTA; malic acid and D-tartaric acid; citric acid and CyDTA; and citric acid and fumaric acid.

The electrophoresis solution may further contain an additive, a surfactant, a stabilizing agent, and the like, for example. The additive needs to be present in the electrophoresis solution at the time of analysis, for example. Thus, the additive may be added in advance to the electrophoresis solution before analysis, or may be added in advance to the sample solution, for example. In the former case, a solution containing the additive preferably is used as the solution filling the separation capillary channel before analysis, for example. Examples of the separation capillary channel include a capillary tube and a capillary channel. On the other hand, in the latter case, the additive may be added directly to the sample, or may be added in advance to a solvent for diluting a sample, as will be described below, for example. The surfactant and the stabilizing agent also need to be present in the electrophoresis solution at the time of analysis, for example. The surfactant and the stabilizing agent may be added to the electrophoresis solution, the sample solution, and the like in the same manner as described above for the additive, for example.

The additive is not particularly limited, and may be, for example, an anionic group-containing compound, an anionic chaotropic ion, or the like.

The anionic group-containing compound is not particularly limited, and examples thereof include anionic group-containing polysaccharides. The anionic group-containing polysaccharides are not particularly limited, and examples thereof include sulfated polysaccharides, carboxylated polysaccharides, sulfonated polysaccharides, and phosphorylated polysaccharides. Among them, sulfated polysaccharides and carboxylated polysaccharides are preferred. As the sulfated polysaccharides, for example, chondroitin sulfate, heparin, and salts thereof are preferred, and chondroitin sulfate and salts thereof are more preferred. As the carboxylated polysaccharides, for example, alginic acid, hyaluronic acid, and salts thereof are preferred. Examples of the salts include sodium alginate and sodium hyaluronate. Examples of the chondroitin sulfate include chondroitin sulfate A, chondroitin sulfate B, chondroitin sulfate C, chondroitin sulfate D, chondroitin sulfate E, chondroitin sulfate H, and chondroitin sulfate K. One kind of anionic group-containing compound may be used, or two or more kinds of anionic group-containing compounds may be used in combination, for example. The combination of the anionic group-containing compounds and the proportion of each anionic group-containing compound are not particularly limited, and they can be set as appropriate.

The concentration of the anionic group-containing compound in the electrophoresis solution at the time of analysis is not particularly limited, and is, for example, about 0.01 wt % to about 5 wt %, preferably about 0.1 wt % to about 2 wt %. As described above, the anionic group-containing compound may be added in advance to the electrophoresis solution, or may be added in advance to the sample, for example. Thus, in the former case, the concentration of the anionic group-containing compound in the electrophoresis solution is not particularly limited, and the anionic group-containing compound preferably is added so that the concentration thereof is in the above-described range at the time of analysis, for example. In the latter case, the concentration of the anionic group-containing compound in the sample is not particularly limited, and the anionic group-containing compound preferably is added so that the concentration thereof is in the above-described range at the time of analysis, for example.

When the sample solution is subjected to electrophoresis in the presence of the anionic group-containing compound, for example, Hb in the sample solution migrates in the electrophoresis solution in the form of a complex with the anionic group-containing compound. Through this complex formation, it is possible to further improve the analysis accuracy and to further shorten the length (separation length) of the separation capillary channel, for example. Thus, it is possible to further shorten the analysis time, for example.

Chaotropic ions generally are ions that enhance the solubility of hydrophobic molecules in water by disrupting interactions between water molecules and inhibiting the decrease in entropy of water caused by contact with hydrophobic molecules. The anionic chaotropic ion is not particularly limited, and examples thereof include a perchloric acid ion ($ClO_4^-$), a thiocyanic acid ion ($SCN^-$), a trichloroacetic acid ion ($CCl_3COO^-$), a trifluoroacetic acid ion ($CF_3COO^-$), a nitric acid ion ($NO_3^-$), a dichloroacetic acid ion ($CCl_2COO^-$), and halide ions. The halide ions are not particularly limited, and examples thereof include a fluoride ion (F), a chloride ion ($Cl^-$), a bromide ion ($Br^-$), an iodide ion ($I^-$), and an astatide ion ($At^-$). Among them, a bromide ion ($Br^-$) and an iodide ion ($I^-$) are preferred. One kind of chaotropic ion may be used, or two or more kinds of chaotropic ions may be used in combination, for example. The combinations of the chaotropic ions and the proportion of each chaotropic ion are not particularly limited, and they can be set as appropriate.

The electrophoresis solution may contain the anionic chaotropic ion, or may contain at least one of a salt containing the anionic chaotropic ion and a substance that generates the anionic chaotropic ion when ionized, for example. In the present invention, as will be described below, it is preferable that the anionic chaotropic ion is not used or is used at a low concentration, for example. Examples of the salt include acidic salts, neutral salts, and basic salts. The salt containing the anionic chaotropic ion and the substance that generates the anionic chaotropic ion when ionized are not particularly limited, and specific examples thereof include: potassium halides such as potassium iodide and potassium bromide; sodium perchlorate; potassium thiocyanate; potassium trichloroacetate, and potassium trifluoroacetate. Therefore, in the present invention, the anionic chaotropic ion encompasses, for example, the salt containing the anionic chaotropic ion, the substance that generates the anionic chaotropic ion when ionized, and the like. One kind of anionic chaotropic ion may be used, or two or more kinds of anionic chaotropic ions may be used in combination, for example. The combination of the anionic chaotropic ions and the proportion of each anionic chaotropic ion are not particularly limited, and they can be set as appropriate.

As described above, by using the anionic chaotropic ion, the separation accuracy is improved, for example. However, if the electrophoresis is carried out in the presence of a high concentration of anionic chaotropic ion, the amount of heat generated may be increased owing to the increase in the amount of the current. Because of this increase in the amount of heat generated, the separation accuracy of Hb deteriorates and the electrophoretic velocity is reduced, for example.

According to the present invention, as described above, by performing electrophoresis under conditions in which the acidic substance is present in the electrophoresis solution, the separation accuracy of Hb is improved. Thus, for example, even when the concentration of the anionic chaotropic ion is low, it is possible to separate Hb with high accuracy. Therefore, according to the present invention, for example by decreasing the anionic chaotropic ion, the above-described influence thereof on the separation accuracy of Hb and the electrophoretic velocity can be suppressed, so that it is possible to carry out analysis with still higher accuracy.

Preferably, the electrophoresis solution at the time of analysis does not contain the anionic chaotropic ion or contains the anionic chaotropic ion at a relatively low concentration, for example. Specifically, the concentration of the anionic chaotropic ion in the electrophoresis solution at the time of analysis is, for example, 1 to 3000 mmol/l, preferably 5 to 100 mmol/l, and more preferably 10 to 50 mmol/l. The anionic chaotropic ion may be added in advance to the electrophoresis solution so that the concentration thereof is in the above-described range at the time of analysis, or may be added in advance to the sample, for example.

The surfactant is not particularly limited, and examples thereof include nonionic surfactants. The nonionic surfactants are not particularly limited, and examples thereof include polyoxyethylene isooctylphenyl ether (trade name "Triton (registered trademark) X-100").

The stabilizing agent is not particularly limited, and examples thereof include sodium azide, glutathione, and ethylenediaminetetraacetic acid (EDTA).

The ionic strengths of the electrophoresis solution before and at the time of analysis are not particularly limited. The pH of the electrophoresis solution is not particularly limited, and is, for example, 4.5 to 6, preferably 4.5 to 5.5.

The method of the present invention preferably is carried out by introducing a sample solution to the electrophoresis solution and then performing electrophoresis, for example. The sample solution is a sample containing Hb. The sample may be a sample derived from a living organism, or a sample that contains a commercially available product containing Hb, for example. Examples of the sample derived from a living organism include blood samples, and specific examples thereof include substances containing blood cells, such as whole blood and blood cell fractions. The sample solution may be a sample itself collected from a living organism, or a diluted sample obtained by diluting the collected sample with a solvent, for example.

The blood samples are not particularly limited, and examples thereof include hemolyzed samples obtained by hemolyzing the substances containing blood cells. The hemolyzing treatment is not particularly limited, and examples thereof include an ultrasonic treatment, a freezing and thawing treatment, a pressure treatment, an osmotic pressure treatment, and a surfactant treatment. Among them, the osmotic pressure treatment is preferred. The osmotic pressure treatment is not particularly limited, and may be carried out by treating the substance containing blood cells with a hypotonic solution or the like, for example. The hypotonic solution is not particularly limited, and examples thereof include water and buffer solutions. The buffer solutions are not particularly limited, and may contain the above-described buffer, additive, and the like, for example.

The solvent used for diluting the sample is not particularly limited, and examples thereof include water, physiological saline, and buffer solutions. The buffer solutions are not particularly limited, and may contain the above-described separation enhancing agent, buffer, additive, surfactant, stabilizing agent, and the like, for example.

As described above, in the case where the separation enhancing agent is added to the sample solution, the separation enhancing agent may be added when performing a hemolyzing treatment or when diluting the sample solution, for example. In the former case, for example, the separation enhancing agent may be added in advance to the hypotonic solution used for an osmotic pressure treatment. In the latter case, for example, the separation enhancing agent may be added in advance to the solvent used for diluting the sample. In the cases where the buffer, the additive, the surfactant, and the stabilizing agent are added to the sample, the above description with regard to the case where the separation enhancing agent is added also applies, for example.

The ionic strength of the sample solution is not particularly limited. The pH of the sample solution is not particularly limited, and it preferably is 4.5 to 6, more preferably 4.5 to 5.5, for example.

When changing the pH of the electrophoresis solution by adding the sample solution thereto, it is preferable that the difference between the pH of the sample solution and the pH of the electrophoresis solution is small. The difference is, for example, 0 to 0.3, preferably 0 to 0.1. The pH of the electrophoresis solution is the pH thereof either before or at the time of analysis, for example, and preferably is the pH of the electrophoresis solution at the time of analysis.

The difference between the pHs may be adjusted by adding the buffer to the sample solution or, as described above, by adding the buffer to the electrophoresis solution before analysis, for example. The latter is preferred. The difference between the pH of the sample solution adjusted using the separation enhancing agent only and the pH of the electrophoresis solution at the time of analysis is, for example, 0.3 or more. However, it is preferable to adjust the difference between these pHs to less than 0.3 by adding the buffer.

The Hb is not particularly limited, and examples thereof include: various types of glycated hemoglobin such as hemoglobin A1a (HbA1a), hemoglobin A1b (HbA1b), stable hemoglobin A1c (stable A1c, s-A1c), and labile hemoglobin A1c (labile A1c, L-A1c); modified hemoglobin such as carbamylated hemoglobin (carbamylated Hb) and acetylated hemoglobin (acetylated Hb): mutant-type hemoglobin such as hemoglobin S (HbS), hemoglobin C (HbC), hemoglobin M (HbM), and hemoglobin H (HhH); normal hemoglobin (HbA0): fetal hemoglobin (HbF); and HbA2. According to the present invention, for example, it is possible to separate and detect HbA1c and other types of Hb with high accuracy and in a short time. Therefore, it is preferable that a target substance to be analyzed by the present invention contains HbA1c, more preferably HbA1c and modified Hb, for example.

Not only the above-listed various types of Hb but also other components may be the target substances to be analyzed by the present invention. The other components are not particularly limited, and examples thereof include albumin (A1b), globulins ($\alpha 1$, $\alpha 2$, $\beta$, $\gamma$ globulins), fibrinogen, glucose, and glycated albumin.

In the method of the present invention, separation of Hb by electrophoresis may be carried out in a separation capillary channel, for example. In this case, the electrophoresis also is referred to as capillary electrophoresis. The method preferably is carried out by a continuous sample introduction method, for example. The continuous sample introduction method generally is a method for introducing a sample solution containing Hb continuously to the separation capillary channel.

The separation capillary channel is not particularly limited, and examples thereof include a capillary tube and a capillary channel formed on a substrate such as a microchip. Therefore, the method may be configured so that, for example, the separation capillary channel is formed on a microchip and the electrophoresis is microchip electrophoresis. Also, the method may be configured so that, for example, the separation capillary channel is a capillary tube and the electrophoresis is capillary electrophoresis.

In the method of the present invention, a capillary tube, a microchip provided with a capillary channel, or the like, for example, can be used as a device provided with the separation capillary channel. The device provided with the separation capillary channel may be self-produced, or a commercially available product may be used as the device, for example.

First, the capillary tube will be described below. It is to be noted, however, that the present invention is by no means limited by the following description.

The inner diameter of the capillary tube is not particularly limited, and is, for example, 10 to 200 µm, preferably 25 to 100 µm. The length of the capillary tube is not particularly limited, and is, for example, 10 to 1000 mm, preferably 15 to 300 mm.

The material of the capillary tube is not particularly limited, and examples thereof include glass and polymers. As the capillary tube, a commercially available product may be used, for example. The glass is not particularly limited, and examples thereof include synthesized quartz glass, fused silica, and borosilicate glass. The polymer is not particularly limited, and specific examples thereof include poly-methyl methacrylate (PMMA), polycarbonate (PC), polystyrene (PS), polyethylene (PE), polytetrafluoroethylene (PTFE), polyetheretherketone(PEEK), cycloolefin polymer (COP), polydimethylsiloxane (PDMS), and polylactic acid.

The inner wall of the capillary tube may be coated with a cationic group-containing coating agent or an anionic group-containing coating agent, for example.

In relation to the cationic group-containing coating agent, it is possible to use a compound containing a cationic group(s) and a reaction group(s), for example. Examples of the reaction group include silyl groups (e.g., alkylsilyl groups and alkoxysilyl groups), alkoxy groups, and halogen groups. Examples of the alkoxy groups include a methoxy group and an ethoxy group. Examples of the halogen groups include a fluoro group, a bromo group, a chloro group, fluorine, and an iodine group, and among them, a chloro group is preferred. For example, when the capillary tube is made of glass as described above, it is preferred to use a compound containing a cationic group(s) and silicon (silylating agent) as the cationic group-containing coating agent, for example. The cationic group may be, for example, an amino group, an ammonium group, or the like. The cationic group-containing coating agent preferably is a silylating agent containing either one of an amino group and an ammonium group as the cationic group, for example. The amino group may be any of primary, secondary, and tertiary amino groups. By using the cationic group-containing silylating agent as the cationic group-containing coating agent, it is possible to further improve the analysis accuracy, for example.

Examples of the cationic group-containing silylating agent include N-(2-diaminoethyl)-3-propyltrimethoxysilane, aminophenoxy dimethyl vinylsilane, 3-aminopropyl diisopropyl ethoxysilane, 3-aminopropyl methylbis(trimethylsiloxy)silane, 3-aminopropyl pentamethyldisiloxane, 3-aminopropyl silanetriol, bis(P-aminophenoxy)dimethylsilane, 1,3-bis(3-aminopropyl)tetramethyldisiloxane, bis(dimethylamino)dimethylsilane bis(dimethylamino)vinylmethylsilane, bis(2-hydroxyethyl)-3-aminopropyltriethoxysilane, 3-cyanopropyl (diisopropyl)dimethylaminosilane, (aminoethylaminomethyl)phenylethyltrimethoxysilane, N-methylaminopropyl triethoxysilane, tetrakis(diethylamino)silane, tris(dimethylamino)chlorosilane, and tris(dimethylamino)silane.

As the cationic group-containing silylating agent, it is possible to use one in which a silicon atom is substituted with titanium or zirconium, for example. One kind of cationic group-containing silylating agent may be used alone, or two or more kinds of cationic group-containing silylating agents may be used in combination, for example.

In the case where the cationic group-containing silylating agent is used, the coating of the inner wall of the capillary tube therewith can be carried out in the following manner, for example. First, the silylating agent is dissolved or dispersed in an organic solvent to prepare a treatment solution. Examples of the organic solvent include dichloromethane and toluene. The concentration of the silylating agent in the treatment solution is not particularly limited. The treatment solution is heated while being passed through a capillary tube made of glass. By virtue of this heating, the silylating agent covalently binds to the inner wall of the capillary tube. As a result, the cationic group in the silylating agent is arranged on the inner wall of the capillary tube. Then, the inner wall of the capillary tube is washed with a washing solution. As the washing solution, it is possible to use at least one selected from the group consisting of organic solvents, acid solutions, alkaline solutions, and surfactant solutions, for example. Examples of the organic solvents include dichloromethane, methanol, and acetone. Examples of the acid solution include phosphoric acid solutions. Although this washing is optional, it is preferred to carry out the washing. As the capillary tube whose inner wall is coated with the cationic group-containing silylating agent, a commercially available product may be used.

The anionic group-containing coating agent is not particularly limited, and any of the above-described anionic group-containing compounds can be used, for example. Among them, the compounds containing an anionic group(s) and a reaction group(s) are preferred. Examples of the reaction group include silyl groups (e.g., alkylsilyl groups and alkoxysilyl groups), alkoxy groups, and halogen groups. Examples of the alkoxy groups include a methoxy group and an ethoxy group. Examples of the halogen groups include a fluoro group, a bromo group, a chloro group, fluorine, and an iodine group, and among them, a chloro group is preferred. Examples of the compounds containing an anionic group(s) and a reaction group(s) include compounds containing an anionic group(s) and silicon (silylating agents). As the anionic group-containing coating agent, an anionic group-containing silylating agent is preferred, for example. The anionic group is, for example, a sulfate group, a carboxylic acid group, a sulfonic acid group, a phosphoric acid group, or the like. By using the anionic group-containing silylating agent as the anionic group-containing coating agent, it is possible to further improve the analysis accuracy, for example. In the case where the anionic group-containing silylating agent is used, the coating of the inner wall of the capillary tube therewith can be carried out in the same manner as the coating with the cationic group-containing silylating agent, for example.

Examples of the anionic group-containing silylating agent include chlorosulfonylphenyl ethyltrimethoxysilane and chlorosulfonylphenylethyl trichlorosilane.

In addition to the above-described substances, examples of the anionic group-containing compound include anionic group-containing polysaccharides. As the anionic group-containing polysaccharide, it is possible to use those described above. The coating with a coating agent containing the anionic group-containing polysaccharide also can be performed in the same manner as the coating with the silylating agent, for example. Also, for example, by using an existing method (see Japanese Patent No. 2711112 and the like, for example), it is possible to coat the inner wall through formation of covalent bonds.

In the case where the capillary tube is used, the method of the present invention can be carried out in the following manner, for example.

First, an electrophoresis solution containing the acidic substance is passed through the capillary tube by depressurizing, or pressurizing the electrophoresis solution with a pump or the like. The time for passing through the electrophoresis solution is, for example, 1 to 60 minutes, and the pressure at which the electrophoresis solution is passed through is, for example, 0.05 to 0.1 MPa.

Next, in the set-up in which the electrophoresis solution is present in the capillary tube, the sample solution containing Hb is introduced into the electrophoresis solution. Then, electrophoresis is performed by applying a voltage between electrodes arranged on the respective ends of the capillary tube. The sample solution is introduced from the anode side of the capillary tube. By applying a voltage, an electroosmotic flow is caused in the electrophoresis solution in the capillary tube, so that Hb in the introduced sample solution migrates toward the cathode side of the capillary tube. When the anionic group-containing compound is present in the electrophoresis solution at the time of analysis, for example, the Hb in the introduced sample solution migrates toward the cathode side of the capillary tube in the form of a complex with the anionic group-containing compound. The voltage applied to the capillary tube is, for example, 1 to 30 kV. The migration of the Hb can be detected by an optical method, for example. The detection by the optical method is not particularly limited, and preferably is carried out at a wavelength of 415 nm, for example. The different types of Hb in the sample are separated owing to the difference in their migration speeds. The thus-separated different types of Hb in the sample solution are detected using a detector. In the present embodiment, the length from the starting point of the migration of the sample solution to the detection point by the detector in the separation capillary channel is referred to as the separation length. The separation length in the capillary tube is, for 1.5 example, 10 to 1000 mm, preferably 15 to 300 mm.

Next, the microchip provided with a separation capillary channel will be described below. It is to be noted, however, that the present invention is by no means limited by the following description.

The separation capillary channel formed on the microchip is not particularly limited, and examples thereof include; a capillary channel formed by cutting out a groove in a substrate of the microchip; and a capillary tube embedded in a groove formed in a substrate of the microchip.

The cross-sectional shape of the capillary channel formed by cutting out a groove in a substrate is not limited, and may be, for example, circular, semicircular, or rectangular. The cross-sectional shape is, for example, the cross-sectional shape of the capillary channel when cut perpendicularly to the sample flowing direction. The coating of the inner wall of the capillary channel may be carried out in the same manner as the coating of the inner wall of the capillary tube described above, for example.

The material of the capillary channel formed by cutting out a groove on a substrate is not particularly limited. Examples of the material include glass and polymers. The glass is not particularly limited, and example, thereof include synthesized quartz glass, fused silica, and borosilicate glass. The polymers are not particularly limited, and examples thereof include polymethyl methacrylate (PMMA), cycloolefin polymer (COP), polycarbonate (PC), polydimethylsiloxane (PDMS), polystyrene (PS), polylactic acid, polyethylene (PE), polytetrafluoroethylene (PTFE), and polyetheretherketone (PEEK). Since the capillary channel is formed by cutting out a groove in a substrate, the substrate may be formed of any of these materials.

The material of the capillary tube embedded in a groove formed in a substrate is not particularly limited. Examples of the material include those described above as the examples of the material of the capillary tube. Furthermore, the coating of the inner wall of the embedded capillary tube may be carried out in the same manner as the coating of the inner wall of the capillary tube described above, for example.

In the microchip, the maximum inner diameter of the separation capillary channel is, for example, 10 to 200 µm, preferably 25 to 100 µm. The maximum length of the separation capillary channel is, for example, 0.1 mm to 15 cm, preferably 0.5 mm to 15 cm. The maximum inner diameter of the separation capillary channel formed on the microchip is as follows, for example: in the case where the cross-sectional shape of the separation capillary channel is semicircular, the maximum inner diameter is the diameter of the semicircle; and in the case where the cross-sectional shape of the separation capillary channel is not semicircular, the maximum inner diameter is the diameter of a circle having an area equivalent to the cross-sectional area of a portion having the largest cross-section.

When a separation capillary channel formed on the microchip is used, the method of the present invention can be carried out in the following manner, for example.

As the microchip, a microchip having a substrate in which a separation capillary channel having solution reservoirs at its respective ends is formed is used. Specifically, the substrate has the separation capillary channel and the two solution reservoirs, and both ends of the channel communicate with the solution reservoirs, respectively, and electrodes are arranged so that a voltage can be applied to both ends of the channel. In the substrate, each of the solution reservoirs is a recess formed on the substrate, for example. One of the solution reservoirs serves as an introduction reservoir into which the sample solution is introduced, and the other solution reservoir is a collection reservoir at which the sample solution that has flowed through the separation capillary channel arrives.

The separation capillary channel is filled with an electrophoresis solution containing the acidic substance. The sample solution containing Hb is introduced into the introduction reservoir formed at one end of the separation capillary channel, and thereafter, a voltage is applied between the electrodes arranged at both ends of the separation capillary channel. The voltage is, for example, 0.5 to 10 kV. By this voltage application, the sample solution is caused to migrate toward the collection reservoir formed at the other end of the separation capillary channel. The migration of Hb is detected by an optical method, for example. Detection by the optical method is not particularly limited, and preferably is carried out at a wavelength of 415 nm, for example. The different types of Hb in the sample are separated owing to the difference in their migration speeds. The thus-separated different types of Hb in the sample solution are detected using a detector. The separation length of the separation capillary channel is, for example, 0.1 mm to 15 cm, preferably 0.5 mm to 15 cm. In the above-described manner, it is possible to separate and analyze the different components in the sample solution. By using the microchip, it is possible to further reduce the size of an analyzer, for example.

When the separation capillary channel formed on the microchip is used, the method of the present invention is not limited to the above-described electrophoresis performed by introducing the sample continuously, for example, and may be carried out in the following manner, for example. Unless otherwise stated, processes in the method described below are the same as those in the above-described method.

As the microchip, a microchip having a substrate on which an introduction capillary channel and a separation capillary channel are formed so as to intersect with each in the form of a cross is used. The introduction capillary channel and the separation capillary channel communicate with each other at the intersecting portion. Specifically, the substrate has the introduction capillary channel, the separation capillary channel, and two solution reservoirs; one end of the introduction capillary channel communicates with one of the solution reservoirs; one end of the separation capillary channel communicates with the other one of the solution reservoirs; and both ends of the introduction capillary channel and both ends of the separation capillary channel are provided with electrodes so that a voltage can be applied between each pair of the electrodes. The solution reservoir communicating with the introduction capillary channel is an introduction reservoir into which the sample solution is introduced, and the solution reservoir communicating with the separation capillary channel is a collection reservoir at which the sample solution that has flowed through the separation capillary channel arrives.

The introduction capillary channel and the separation capillary channel are filled with an electrophoresis solution containing the acidic substance. The sample solution containing Hb is introduced into the introduction reservoir formed at one end of the introduction capillary channel, and thereafter, a voltage is applied between the electrodes arranged at both ends of the introduction capillary channel. The voltage is, for example, 0.5 to 10 kV. B this voltage application, the sample solution is caused to migrate to the intersecting portion. Further, a voltage is applied between the electrodes arranged at both ends of the separation capillary channel. The voltage is, for example, 0.5 to 10 kV. By this voltage application, the sample solution is caused to migrate toward the collection reservoir formed at one end of the separation capillary channel. The migration of Hb is detected by an optical method, for example. Detection by the optical method is not particularly limited, and preferably is carried out at a wavelength of 415 nm, for example. The different types of Hb in the sample are separated owing to the difference in their migration speeds. The thus-separated different types of Hb in the sample solution are detected using a detector. In the present embodiment, the length from the intersecting portion, i.e., the starting point of the migration of the sample solution, to the detection point by the detector in the separation capillary channel is referred to as a separation length. The separation length in the separation capillary channel is, for example, 0.1 mm to 15 cm, preferably 0.5 mm to 15 cm. In the above-described manner, it is possible to separate and analyze the different components in the sample solution. By using the microchip, it is possible to further reduce the size of an analyzer, for example.

The analysis kit of the present invention includes the separation enhancing agent according to the present invention, as described above. In addition to the separation enhancing agent, the analysis kit of the present invention further may include an electrophoresis solution, a buffer, an additive, a surfactant, a stabilizing agent, and the like, for example. The analysis kit of the present invention may further include a separation capillary channel, for example. The separation capillary channel is, for example, the same as described above, and examples thereof include a capillary tube and a capillary channel formed on a substrate. Examples of the latter include a microchip. The analysis kit of the present invention may further include instructions for use, for example.

EXAMPLES

Hereinafter, examples of the present invention will be described together with a comparative example. It is to be noted, however, that the present invention is by no means limited by the following examples and comparative example.

Example 1

In the present example, cyclohexanecarboxylic acids, which are the acidic substance, were used as the separation enhancing agents to analyze sample solutions containing carbamylated Hb.

Electrophoresis solutions were prepared according to the composition shown in the following table. Each of the electrophoresis solutions was prepared by, first, preparing an L-tartaric acid-arginine aqueous solution shown below as a buffer solution, and then adding the various components to the buffer solution. In the electrophoresis solutions, the separation enhancing agents respectively were: CyDTA ($pK_{a1}$=2.42, $pK_{a2}$=3.53); 1,1-cyclohexanediacetic acid; 1,2,4-cyclohexanetricarboxylic acid ($pK_{a1}$=2.6, $pK_{a2}$=4.59); and 1,2,3,4,5,6-cyclohexanehexacarboxylic acid monohydrate, which are all the above-described cyclohexanecarboxylic acids. The acid dissociation constants of L-tartaric acid were: $pK_{a1}$=3.02 and $pK_{a2}$=4.54.

TABLE 1

| (Electrophoresis solution: pH 4.8) | |
|---|---|
| Component | Concentration |
| L-tartaric acid-arginine* aqueous solution | 100 mmol/l |
| chondroitin sulfate C | 1.0 w/v % |
| sodium azide | 1 mmol/l |
| Triton (registered trademark) X-100 | 0.01 w/v % |
| propionic acid | 2 mmol/l |
| separation enhancing agent | 2 mmol/l |

*The arginine was added for pH adjustment.

Further, as diluents used for preparing sample solutions, solutions (pH 4.8) were prepared by setting the concentration of each component of the respective electrophoresis solutions to 1.1 times.

Sodium cyanate was added to a Hb control sample (manufactured by BML) so that the concentration thereof was 10 mg/100 mL, and the resultant solution was allowed to react at 37° C. for 2 hours. By this reaction, cyanidation of the Hb was achieved. This reaction solution and each of the diluents were mixed together at a volume ratio of 1:10. Thus, sample solutions (pH 4.8) were prepared.

A microchip made of PMMA and having a separation capillary channel (full length: 35 mm, inner diameter: 50 μm) was used. A 0.01 wt % alginic acid aqueous solution was passed through the separation capillary channel of the microchip to coat the inner wall thereof.

The capillary channel was filled with the electrophoresis solution pressurized to 0.1 MPa (1000 mbar), and then, the sample solution was introduced into the anode side of the capillary channel. A voltage of 1400 was applied between electrodes arranged at both ends of the capillary channel, thus subjecting the sample solution to electrophoresis. Absorbance at 415 nm was measured at a detection point using a spectrophotometer. In the present example, the detection point was a point 20 mm away from the sample solution introduction site toward the cathode side, and the separation length was 20 mm. A graph showing the relationship between the detection time and the absorbance was prepared, and the degree of separation between the peak of stable HbA1c (s-A1c) and the peak of modified Hb (carbamylated Hb in the present example) was calculated using the following equation.

$$\text{Degree of separation} = 1.18 \times (t2-t1)/(p1+p2)$$

t1=the detection time of the peak of the modified Hb
t2=the detection time of the peak of the stable HbA1c
p1=the full width at half maximum* of the peak of the modified Hb
p2=the full width at half maximum* of the peak of the stable HbA1c

* full width at half maximum: the peak width measured at half of the peak height.

Figure 1B:
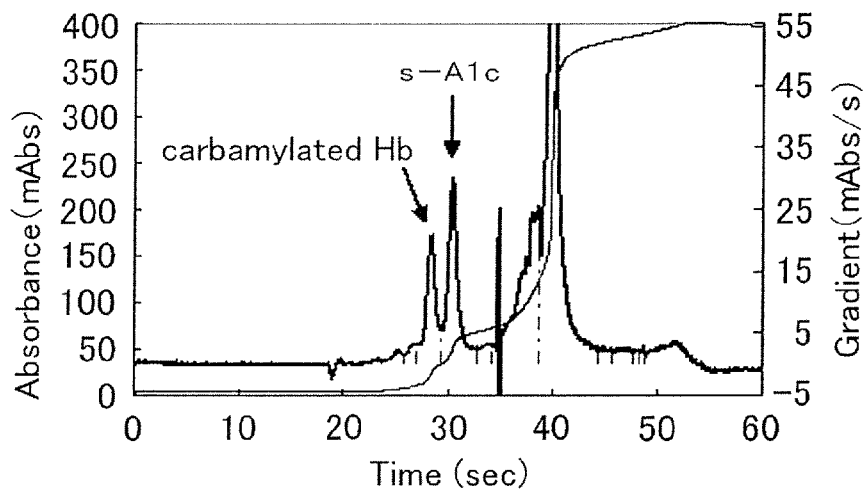
Figure 1C:
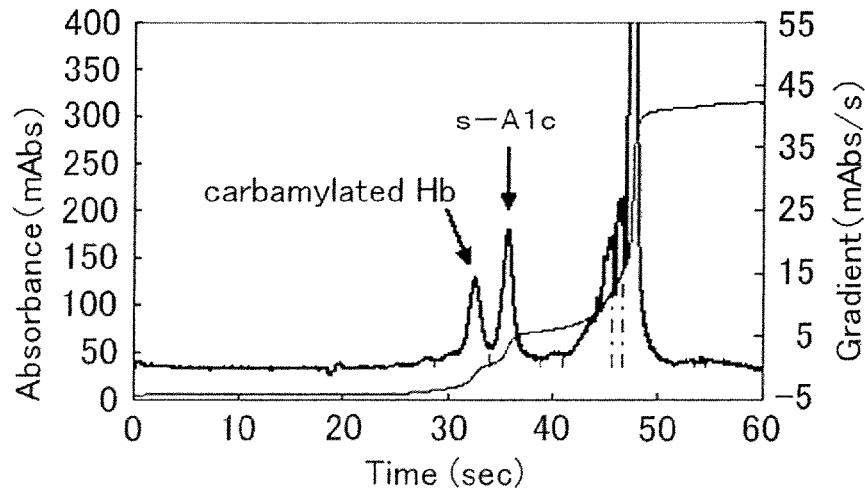

Detection results obtained in Example 1 are shown in the graphs of FIGS. 1A to 1C. FIG. 1A shows the results obtained when L-tartaric acid and CyDTA were added, FIG. 1B shows the results obtained when L-tartaric acid and 1,1-cyclohexanediacetic acid were added, and FIG. 1C shows the results obtained when L-tartaric acid and 1,2,4-cyclohexanetricarboxylic acid were added. In the graphs of FIGS. 1A to 1C, a thick line indicates the absorbance at 415 nm, and a thin line indicates the gradient (the absorbance change rate, mAbs/second). In these graphs, the vertical axis on the left indicates the absorbance at 415 nm (mAbs), the vertical axis on the right indicates the gradient (the absorbance change rate, mAbs/second), and the horizontal axis indicates time (seconds). In these graphs, the peaks indicated with arrows are, from the left, the peak of the modified Hb (carbamylated Hb) and the peak of the stable HbA1c (s-A1c).

As can be seen from FIGS. 1A to 1C, in Example 1, the peaks of the s-A1c and the carbamylated Hb were detected as separate peaks within about 40 seconds from the start of the measurement. The degree of separation was 1.3 in all of the cases where: L-tartaric acid and CyDTA were added (FIG. 1A); L-tartaric acid and 1,1-cyclohexanediacetic acid were added (FIG. 1B); and L-tartaric acid and 1,2,4-cyclohexanetricarboxylic acid were added (FIG. 1C). In particular, as shown in FIGS. 1A and 1B, when L-tartaric acid and CyDTA were added (FIG. 1A) and when L-tartaric acid and 1,1-cyclohexanediacetic acid were added (FIG. 1B), the peaks of the s-A1c and the carbamylated Hb were detected as more distinct separate peaks within about 30 seconds from the start of the measurement. Furthermore, although not shown in the drawing, when 1,2,3,4,5,6-cyclohexanehexacarboxylic acid monohydrate was added, the s-A1c and the carbamylated Hb similarly were detected separately, and the degree of separation was 1.2. In Example 1, the pH of the electrophoresis solutions at the time of analysis was 4.8. As described above, by adding the acidic substances, the separation accuracy of the s-A1c and the carbamylated Hb was improved and the analysis time was shortened.

Example 2

In the present example, instead of the Hb control sample, human whole blood was used, and instead of the sodium cyanate, acetaldehyde was used for aldehydation of Hb. Sample solutions (pH 4.8) were prepared in the same manner as in Example 1, except that the acetaldehyde was added to the human whole blood so that the concentration thereof was 10 mg/100 ml. Analysis was carried out in the same manner as in Example 1, except that the thus-prepared sample solutions were used.

Figure 2:
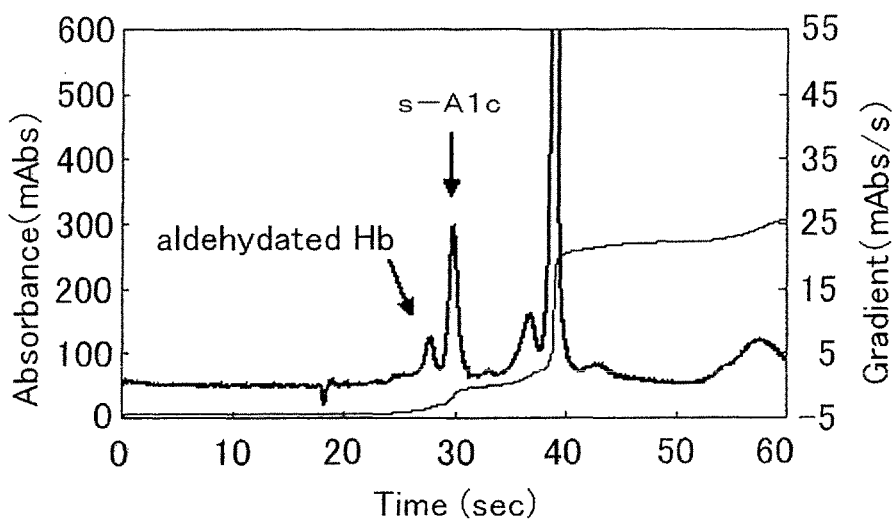
FIG. 2 is a graph showing the results of hemoglobin detection in Example 2.

Detection results obtained when CyDTA was added in Example 2 are shown in the graph of FIG. 2. In the graph of FIG. 2, a thick line indicates the absorbance at 415 nm, and a thin line indicates the gradient (the absorbance change rate, mAbs/second). In the graph of FIG. 2, the vertical axis on the left indicates the absorbance at 415 nm (mAbs), the vertical axis on the right indicates the gradient (the absorbance change rate, mAbs/second), and the horizontal axis indicates time (seconds). In the graph of FIG. 2, the peaks indicated with arrows are, from the left, the peak of modified Hb (aldehydated Hb) and the peak of stable HbA1c (s-A1c).

As shown in FIG. 2, in Example 2, as a result of adding CyDTA, the peaks of s-A1c and aldehydated Hb were detected as separate peaks within about 30 seconds from the start of the measurement. Furthermore, although not shown in the drawing, when the other cyclohexanecarboxylic acids used in Example 1 were added, s-A1c and aldehydated Hb were detected separately as in the case where CyDTA was added. In particular, as shown in FIG. 2, when CyDTA was added, the peaks of the s-A1c and the aldehydated Hb were detected as more distinct separate peaks. In Example 2, the pH of the electrophoresis solutions at the time of analysis was 4.8. As described above, by adding the acidic substance, the separation accuracy of the s-A1c and the aldehydated Hb was improved.

Example 3

In the present example, instead of the Hb control sample, human whole blood was used, and instead of the sodium cyanate, glucose was used for glycation of Hb. Sample solutions (pH 4.8) were prepared in the same manner as in Example 1, except that the glucose was added to the human whole blood so that the concentration thereof was 1500 mg/100 ml. Analysis was carried out in the same manner as in Example 1, except that the thus-prepared sample solutions were used.

Figure 3:
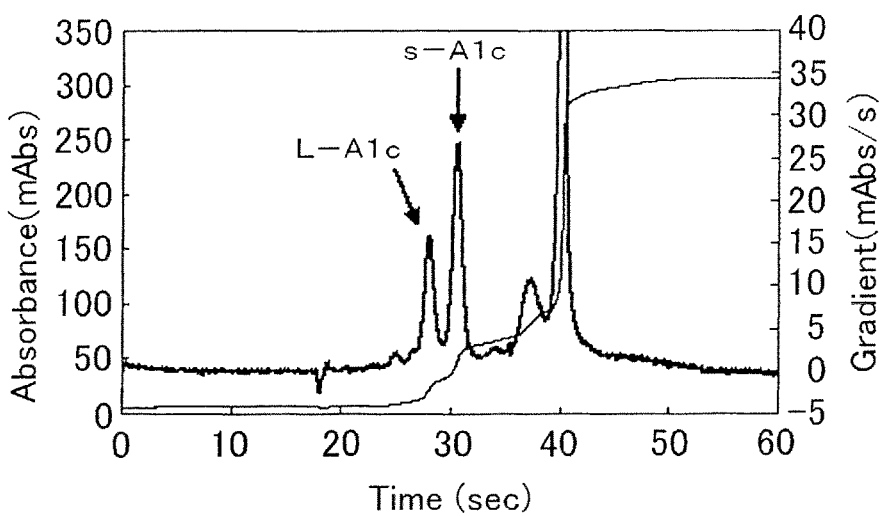
FIG. 3 is a graph showing the results of hemoglobin detection in Example 3.

Detection results obtained when CyDTA was added in Example 3 are shown in the graph of FIG. 3. In the graph of FIG. 3, a thick line indicates the absorbance at 415 nm, and a thin line indicates the gradient (the absorbance change rate, mAbs/second). In the graph of FIG. 3, the vertical axis on the left indicates the absorbance at 415 nm (mAbs), the vertical axis on the right indicates the gradient (the absorbance change rate, mAbs/second), and the horizontal axis indicates time (seconds). In the graph of FIG. 3, the peaks indicated with arrows are, from the left, the peak of labile A1c (L-A1c) and the peak of stable A1c (s-A1c).

As shown in FIG. 3, in Example 3, as a result of adding CyDTA, the peaks of the s-A1c and the labile A1c were detected as separate peaks within about 30 seconds from the start of the measurement. Furthermore, although not shown in the drawing, when the other cyclohexanecarboxylic acids used in Example 1 were added, s-A1c and labile A1c were detected separately as in the case where CyDTA was added. In particular, as shown in FIG. 3, when CyDTA was added, the peaks of the s-A1c and the labile A1c were detected as more distinct separate peaks. In Example 3, the pH of the electrophoresis solutions at the time of analysis was 4.8. As described above, by adding the acidic substance, the separation accuracy of the s-A1c and the labile A1c was improved.

Example 4

In the present example, analysis was carried out in the same manner as in Example 1, except that, as the separation enhancing agent, L-glutamic acid ($pK_{a1}$=2.18, $pK_{a2}$=4.20) was used instead of the cyclohexanecarboxylic acids.

Figure 4:
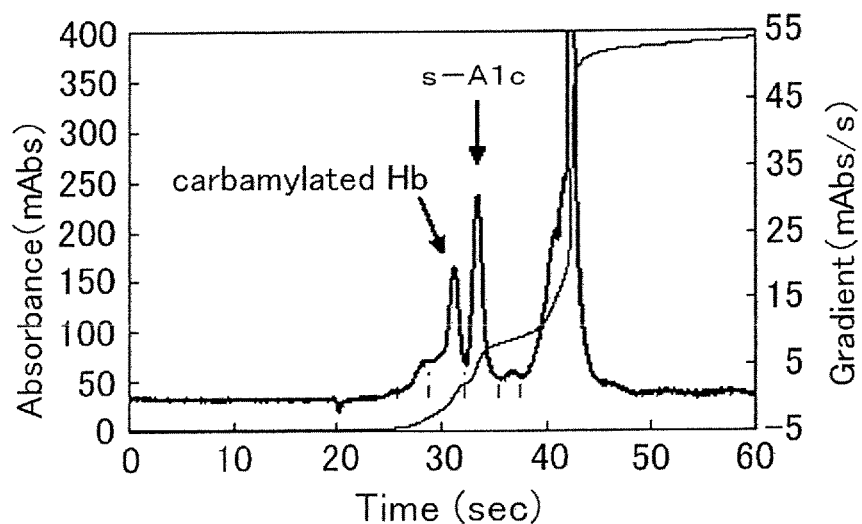
FIG. 4 is a graph showing the results of hemoglobin detection in Example 4.

Detection results obtained in Example 4 are shown in the graphs of FIG. 4. In the graph of FIG. 4, a thick line indicates the absorbance at 415 nm, and a thin line indicates the gradient (the absorbance change rate, mAbs/second). In the graph of FIG. 4, the vertical axis on the left indicates the absorbance at 415 nm (mAbs), the vertical axis on the right indicates the gradient (the absorbance change rate, mAbs/second), and the horizontal axis indicates time (seconds). In the graph of FIG. 4, the peaks indicated with arrows are, from the left, the peak of modified Hb (carbamylated Hb) and the peak of stable HbA1c (s-A1c).

As shown in FIG. 4, in Example 4, as a result of adding L-glutamic acid, the peaks of the s-A1c and the carbamylated Hb were detected as separate peaks within about 35 seconds from the start of the measurement. The degree of separation was 1.24. In Example 4, the pH of the electrophoresis solution at the time of analysis was 4.8. As described above, by adding the acidic substance, the separation accuracy of the s-A1c and the carbamylated Hb was improved and the analysis time was shortened.

Example 5

In the present example, an electrophoresis solution was prepared according to the composition shown in Table 1, except that the separation enhancing agent was not added and D-tartaric acid was added as the acidic substance so that the concentration thereof was 100 mmol/l instead of L-tartaric acid as a buffer. Furthermore, based on the composition of the electrophoresis solution, a diluent was prepared in the same manner as in Example 1. Analysis was carried out in the same manner as in Example 1, except that the thus-prepared electrophoresis solutions and diluents were used. The acid dissociation constants of D-tartaric acid were: $pK_{a1}$=2.82 and $pK_{a2}$=3.96.

Figure 5:
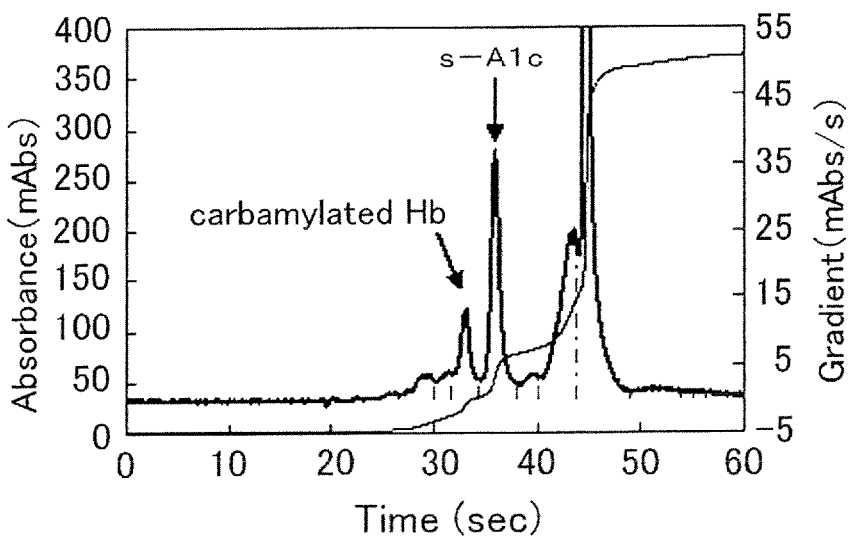
FIG. 5 is a graph showing the results of hemoglobin detection in Example 5.

Detection results obtained in Example 5 are shown in the graph of FIG. 5. In the graph of FIG. 5, a thick line indicates the absorbance at 415 nm, and a thin line indicates the gradient (the absorbance change rate, mAbs/second). In the graph of FIG. 5, the vertical axis on the left indicates the absorbance at 415 nm (mAbs), the vertical axis on the right indicates the gradient (the absorbance change rate, mAbs/second), and the horizontal axis indicates time (seconds). In the graph of FIG. 5, the peaks indicated with arrows are, from the left, the peak of modified Hb (carbamylated Hb) and the peak of stable HbA1c (s-A1c).

As shown in FIG. 5, in Example 5, as a result of adding D-tartaric acid, the peaks of the s-A1c and the carbamylated Hb were detected as separate peaks within about 35 seconds from the start of the measurement.

In Example 5, the pH of the electrophoresis solution at the time of analysis was 4.8. As described above, by adding D-tartaric acid, the analysis accuracy of the s-A1c and the carbamylated Hb was improved and the analysis time was shortened.

Comparative Example 1

In the present example, electrophoresis solutions were prepared according to the composition shown in Table 1, except that the separation enhancing agent was not added and a 100 mmol/l glutaric acid-arginine aqueous solution or a 100 mmol/l propionic acid-arginine aqueous solution was used as a buffer solution instead of the L-tartaric acid-arginine aqueous solution. Furthermore, based on the composition of these electrophoresis solutions, diluents were prepared in the same manner as in Example 1. Analysis was carried out in the same manner as in Example 1, except that the thus-prepared electrophoresis solutions and diluents were used. Glutaric acid has two carboxyl groups, and the acid dissociation constants of these carboxyl groups are $pK_{a1}$=4.13 and $pK_{a2}$=5.01, respectively. Furthermore, propionic acid has only one carboxyl group, and the acid dissociation constant of the carboxyl group is pKa=4.86.

Figure 6A:
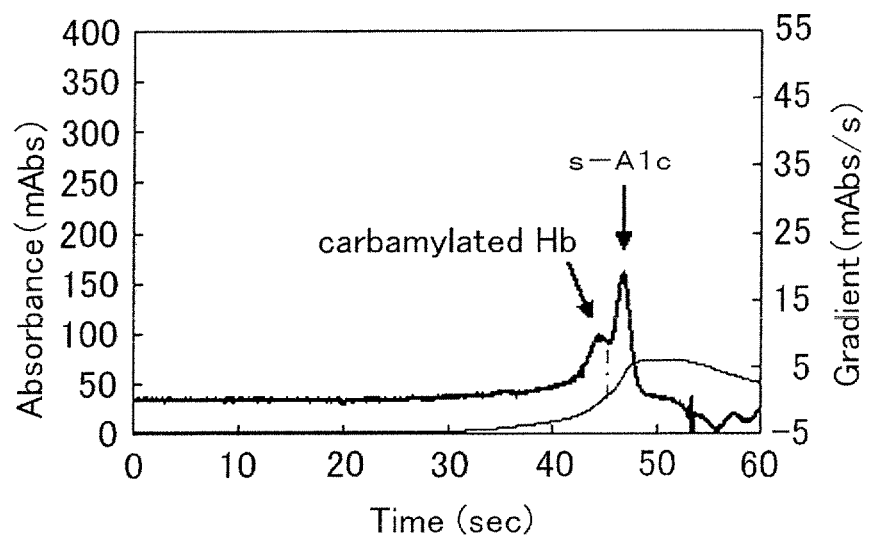
FIGS. 6A and 6B are graphs showing the results of hemoglobin detection in Comparative Example 1.
Figure 6B:
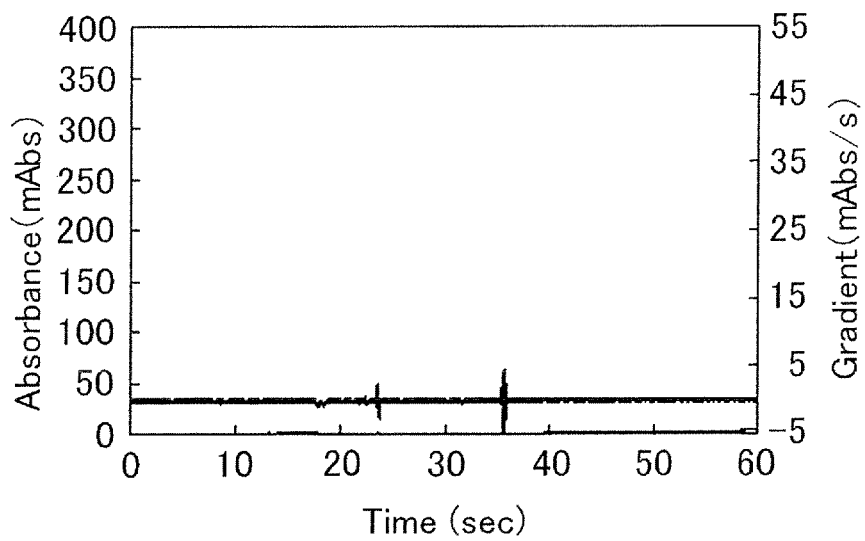

Detection results obtained in Comparative Example 1 are shown in the graphs of FIGS. 6A and 6B. FIG. 6A shows the results obtained when the glutaric acid-arginine aqueous solution was used, and FIG. 6B shows the results obtained when the propionic acid-arginine aqueous solution was used In the graphs of FIGS. 6A and 6B, a thick line indicates the absorbance at 415 nm, and a thin line indicates the gradient (the absorbance change rate, mAbs/second). In both the graphs, the vertical axis on the left indicates the absorbance at 415 nm (mAbs), the vertical axis on the right indicates the gradient (the absorbance change rate, mAbs/second), and the horizontal axis indicates time (seconds). In the graph of FIG. 6A, the peaks indicated with arrows are, from the left, modified Hb (carbamylated Hb) and stable HbA1c (s-A1c).

As shown in FIG. 6A, when the glutaric acid-arginine aqueous solution was used, the peaks of the s-A1c and the carbamylated Hb were low and broad, and the s-A1c and the carbamylated Hb could not be detected separately. The degree of separation was 0.5. As shown in FIG. 6B, when the propionic acid-arginine aqueous solution was used, no peak was detected. In Comparative Example 1, the pH of the electrophoresis solutions at the time of analysis was 5.0. As described above, in the presence of the glutaric acid or the propionic acid, it was not possible to detect the s-A1c and the carbamylated Hb separately.

As is apparent from the results obtained in Examples 1 to 5 and Comparative Example 1, by subjecting a sample solution to electrophoresis in the presence of the acidic substance, the separation accuracy of Hb was improved and the analysis time was shortened. In particular, the separation accuracy between stable HbA1c (s-A1c) and modified Hb or labile A1c was improved.

As described above, according to the present invention, it is possible to improve the analysis accuracy of Hb such as HbA1c and modified hemoglobin and shorten the analysis time, for example. The present invention is applicable to all the fields in which hemoglobin is analyzed, such as clinical tests, biochemical tests, and medical research, for example. The use of the present invention is not limited, and the present invention can be applied to a wide range of fields.

It should be understood that the foregoing discussions and examples merely present a detailed description of certain exemplary embodiments. It should therefore be apparent to those of ordinary skill in the art that modifications and equivalents can be made without departing from the spirit and scope of the invention. All journal articles, other references, patents and patent applications that are identified in this application are incorporated by reference in their entireties.

What is claimed is:

1. A method for analyzing hemoglobin in a sample solution containing hemoglobin by electrophoresis, the method comprising:
   performing electrophoresis of the sample solution under conditions in which an add substance having two or more carboxyl groups is present in an electrophoresis solution having a pH of 4.5 to 6,
wherein
   the electrophoresis solution comprises a buffer and a separation enhancing agent, the separation enhancing agent comprising the acid substance;
   a difference obtained by subtracting a second acid dissociation constant ($pK_{a2}A$) of the acid substance in the separation enhancing agent from an acid dissociation constant ($pK_aB$) of the buffer responsible for its buffer capacity is 0.2 or more;
   separation of hemoglobin by the electrophoresis is carried out in a separation capillary channel; and
   at least two of the carboxyl groups of the acid substance each have an acid dissociation constant ($pK_{a1}A$ and $pK_{a2}A$) lower than a pH of the electrophoresis solution at the time of analysis,
wherein the acid substance (A) is L-glutamic acid or (B) comprises a cyclohexane ring or (C) comprises two or more carboxyl groups where one of the carboxyl groups has a second dissociation constant ($pK_{a2}$) in the range of 2 to 4.

2. The method according to claim 1, wherein the two or more carboxyl groups of the acid substance each have an acid dissociation constant ($pK_{a1}A$ and $pK_{a2}A$) that is lower than the pH of the electrophoresis solution at the time of analysis by 0.7 or more.

3. The method according to claim 1, wherein the acid dissociation constant ($pK_aB$) of the buffer responsible for its buffer capacity is equal to or greater than a value obtained by subtracting 0.3 from the pH of the electrophoresis solution at the time of analysis.

4. The method according to claim 1, wherein a difference between a pH of the sample solution containing hemoglobin and the pH of the electrophoresis solution is less than 0.3.

5. The method according to claim 1, wherein the acid substance comprises a cyclohexane ring.

6. The method according to claim 5, wherein the acid substance is at least one selected from the group consisting of trans-1,2-cyclohexanediamine-N,N,N'N'-tetraacetic acid (CyDTA); 1,1-cyclohexanediacetic acid; (1α,2α,4α)-1,2,4-cyclohexanetricarboxylic acid; and 1,2,3,4,5,6-cyclohexanehexacarboxylic acid monohydrate.

7. The method according to claim 1, wherein the method is carried out by using a continuous sample introduction method for introducing the sample solution containing hemoglobin continuously to the separation capillary channel.

8. The method according to claim 1, wherein the separation capillary channel is formed on a microchip, and the electrophoresis is microchip electrophoresis.

9. The method according to claim 1, wherein the separation capillary channel is a capillary tube, and the electrophoresis is capillary electrophoresis.

10. The method according to claim 1, wherein the hemoglobin is hemoglobin A1c.

11. The method according to claim 10, wherein the hemoglobin A1c is at least one selected from the group consisting of stable hemoglobin A1c and labile hemoglobin A1c.

12. The method according to claim 1, wherein the hemoglobin is at least one kind of modified hemoglobin selected from the group consisting of carbamylated hemoglobin, aldehydated hemoglobin, and acetylated hemoglobin.

13. The method according to claim 1, wherein the acid substance is L-glutamic acid.

14. The method according to claim 1, wherein the acid substance comprises two or more carboxyl groups where one of the carboxyl groups has a second dissociation constant ($pK_{a2}$) in the range of 2 to 4.

* * * * *